United States Patent [19]
Yachia et al.

[11] Patent Number: 5,246,445
[45] Date of Patent: Sep. 21, 1993

[54] DEVICE FOR THE TREATMENT OF CONSTRICTED DUCTS IN HUMAN BODIES

[75] Inventors: Daniel Yachia, Natania; Mordechay Beyar, Tel Aviv, both of Israel

[73] Assignee: InStent Inc., Eden Prairie, Minn.

[21] Appl. No.: 827,031

[22] Filed: Jan. 24, 1992

Related U.S. Application Data

[63] Continuation of Ser. No. 281,179, Oct. 31, 1991.

[30] Foreign Application Priority Data

Apr. 19, 1990 [IL] Israel ............................... 94138

[51] Int. Cl.⁵ .................. A61M 5/00; A61B 17/00
[52] U.S. Cl. ................... 606/108; 606/104; 623/1
[58] Field of Search ........... 606/108, 191, 195, 198, 606/200, 151–154; 623/1, 12; 128/858

[56] References Cited

U.S. PATENT DOCUMENTS

| | | |
|---|---|---|
| 4,768,507 | 9/1988 | Fischell et al. ............ 606/108 |
| 4,878,906 | 11/1989 | Lindemann et al. ........ 606/108 |
| 4,913,141 | 4/1990 | Hillstead .................... 606/108 |
| 5,147,370 | 9/1992 | McNamara et al. . |

OTHER PUBLICATIONS

E. J. G. Milroy et al., "A New Treatment for Urethral Strictures": A Permanently Implanted Urethral Stent Journal of Urology, vol. 141, May, 1989 pp. 1120–1122. Journal of Urology, vol. 141, May, 1989 pp. 1120–1122.

*Primary Examiner*—C. Fred Rosenbaum
*Assistant Examiner*—William Lewis
*Attorney, Agent, or Firm*—Cowan, Liebowitz & Latman

[57] ABSTRACT

This invention is directed to a system for implanting a device to open constrictions in corpeal conduits, which comprises (a) an elongated tubular member and (b) a spatial spiral of elongate axial extension wound of thin wire and having attachment means at each end, said spiral being positioned on and concentric to said elongated tubular member, said spiral being in a constricted condition such that its lateral profile is smaller than it would be if said spiral were not constricted.

12 Claims, 7 Drawing Sheets

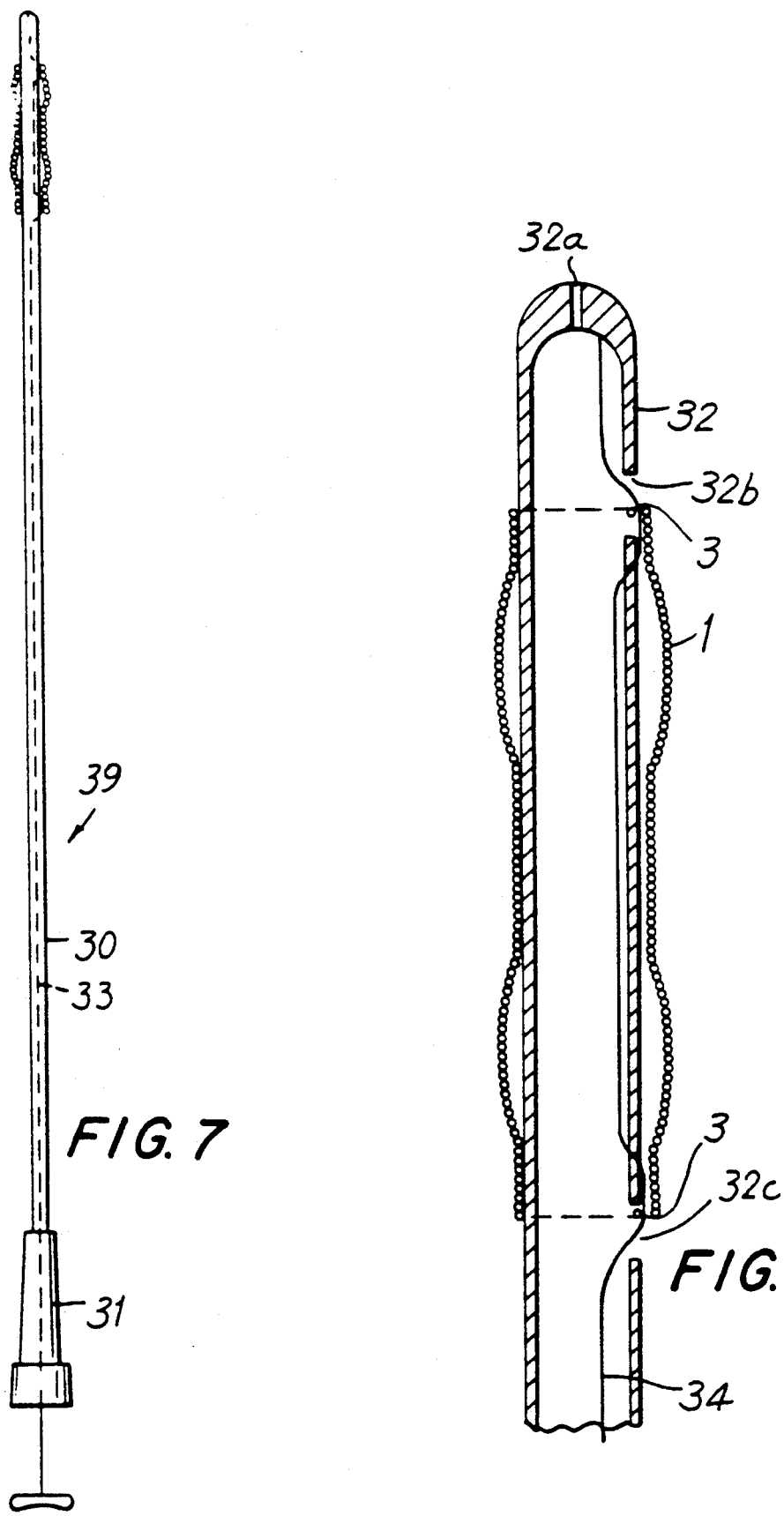

DEVICE FOR THE TREATMENT OF CONSTRICTED DUCTS IN HUMAN BODIES

This is a continuation of copending application Ser. No. 07/781,174 filed on Oct. 31, 1991.

FIELD OF THE INVENTION

This invention is directed to devices for the treatment of constricted ducts in human bodies. More particularly, this invention is directed to intravascular, urethral, ureteral, bronchial, oesophageal, and biliary stents and systems for implanting them.

BACKGROUND OF THE INVENTION

Urethral strictures can be congenital or acquired. Acquired urethral stricture is common in men but rare in women. Most acquired strictures are due to infection or trauma. Apart from infections caused by venereal diseases, infection from long term use of urethral catheters and the use of large caliber instruments inserted for medical uses into the urethra causes trauma to the urethra. External trauma, e.g., pelvic bone fractures or saddle injuries, can also cause urethral strictures. These narrowings restrict the urine flow. In chronic cases the bladder muscle becomes hypertrophic, and later an increase in the residual urine may develop in the bladder. Prolonged obstruction may cause incompetence of the outflow contom mechanism resulting in incontinence or high pressures in the bladder resulting in kidney damage and renal failure. Residual urine may be a predisposing factor for urinary infections which include prostatic infections, urethral abscess and also bladder stones.

Urethral strictures can be managed with palliative treatments such as dilatations of the urethra, which are not curative, because dilatation fractures the scar tissue and temporarily enlarges the lumen. As healing occurs, the scar tissue reform.

Visually controlled internal urethrotomy is also used in the treatment of urethral strictures. However, in most cases the stricture reoccurs and the procedure has to be repeated.

Plastic surgical repair of the stricture is a meticulous and complicated procedure. However, this procedure has a high recurrence of urethral strictures, and because of the lack of enough experienced surgeons for reconstructive surgery, the majority of cases are managed by non-curative methods.

An intraurethral device designed for urethral strictures made of an expandable tubular mesh is described by E. J. G. Milroy et al., in an article which appeared in the Journal of Urology (Vol. 141, May 1989). The device is inserted in a stenotic duct and keeps the lumen open as its inner diameter is as large as the duct lumen. Due of its sharp ends, this device cannot be inserted into the mobile parts of the urethra because of severe pain and the danger of perforations of the urethra. This device becomes incorporated into the urethral wall within 3 to 6 months of its insertion, becoming a permanent device and necessitating surgical intervention for its removal.

Bladder outlet obstruction is one of the most commonly encountered disorders in urology. The most frequently occurring anatomical cause of bladder outlet obstruction in males is enlargement of the prostate gland, either by benign hypertrophy or cancer. The prostate is a chestnut-sized gland lying inferior to the bladder and surrounding approximately the first inch of the urethra. As males age, the prostate commonly enlarges—without necessarily being malignant—and tends to gradually narrow or constrict its central opening and thus exert radial, inwardly directed pressure on the prostatic urethra. This condition, known as benign prostatic hyperplasia, can cause a variety of obstructive symptoms, including urinary hesitancy, straining to void, and decreased size and force of the urinary stream. As the condition gradually worsens, there may be total closure of the urethra and concomitant complete urinary retention, possibly leading to renal failure.

When intervention is indicated, there has heretofore been no widely accepted alternative to surgery. The preferred surgical procedure is the transurethral resection, wherein a resectoscope is inserted through the external opening of the urethra, and an electrosurgical loop is employed to cut away sections of the prostate gland from within the prostatic urethra. Another surgical intervention is open surgical removal of the gland performed through an abdominal incision. However, many patients are poor candidates for surgery.

Another treatment is balloon dilatation of the prostate. According to that technique expansion of the prostatic urethra up to a diameter of 3 to 4 cm results in tearing of the prostate comissures while keeping the prostatic urethra open. The long time efficacy of this treatment has not yet been established.

The aforementioned treatments are not applicable in the case of poor operative risk patients because these surgical steps are performed under general or regional anaesthesia and incapacitate a patient for a certain period. Moreover, surgery does not always result in full relief. In some cases a seriously ill patient has to rely on a perpetually worn catheter.

A number of devices have been suggested which are said to provide relief of the effects of prostate hypertrophy. European Patent Application No. 027486, which is based on U.S. patent application Ser. No. 939,754, filed Dec. 9, 1986, describes an expansion catheter which is transurethrally inserted and is placed in a stenotic prostatic urethra. The insertion is performed with the aid of a special balloon catheter which is removed after insertion, leaving in the urethra an expanded stent which ensures the maintenance of the open lumen of the prostatic lumen.

A full description of pathology of male urethra is given by K. A. Kropp in an article "Strictures of the Male Urethra", published by Year Book Medical Publisher, Chicago, London, and in Campbell's Urology, 5th Edition, published by W. B. Saunders Co., Philadelphia, Pa. U.S.A., which article is incorporated herein by reference.

SUMMARY OF THE INVENTION

The present invention relates to a device intended for use in dealing with constrictions in ducts in the human body to relieve the possible pathological results of such stenoses. One of the frequently occurring such constrictions is that of the male urethra due to urethrostenosis of inflammatory or traumatic origin or benign or malignant enlargement of the prostate. However, the device of this invention is not intended exclusively for such use but is useful to treat restriction or constriction of other body ducts. Other frequent strictures for which the device according to the invention is useful include those of the ureters, blood vessels, biliary ducts, intestines, oesophagus, and airways of the lungs. The attending physician will decide to what extent the new device can be employed in treatment of stenotic conditions of a duct in a human body.

The invention will be described below, using the conditions resulting from prostatic urethral constriction as an example for use of the device. However, as stated above, the invention is not limited to this use.

The invention further relates to means and methods for introducing the device into and depositing it in the urethra (or other duct), to ensure free and unimpeded flow of urine from the bladder to the natural outlet, or of whatever other fluid into or out of the respective conduit.

Treatment by means of the device of this invention can also be applied to all kinds of urethral stricture caused by other causes, such as infections, inflammations, and trauma.

Another application of the different design of the device is to open the prostatic urethral lumen to a very large diameter (30 to 40 mm diameter), resulting in devulsion of the prostatic commissure and application of pressure atrophy on the gland tissue. This method results in opening of the prostatic lumen and freeing of the patient from the obstruction caused by the pressure of the gland. Also, this method has an advantage on the balloon dilatation of the prostate as it does not require anaesthesia and it acts for a long period (up to a few days) and causes pressure atrophy—a method which cannot be applied in the balloon dilatation of the prostate because of the short time of the procedure.

OBJECTS OF THE INVENTION

It is an object of this invention to provide a device and a delivery system for the treatment of constricted ducts in human bodies.

It is also object of this invention to provide an intravascular stent to open and/or maintain the opening in a constricted body duct, particularly the male urethra, cardiovascular system, ureters, biliary ducts, oesophageal, and bronchial system.

It is a further object of the invention to provide a helically wound coil having attachments at the respective ends and an insertion means for inserting said coil into a constricted body duct.

These and other objects of the invention will become more apparent in the discussion below.

BRIEF DESCRIPTION OF THE DRAWINGS

FIGS. 6, 6a, 7, and 7a represent lateral views of insertion systems according to the invention.

DETAILED DESCRIPTION OF THE INVENTION

The new device according to the invention is a spatial spiral of elongate axial extension wound helically and tightly of thin wire and having attachment means at each end. It is preferred that the windings of the device are non-uniform to the extent that at one or more locations intermediate of the two ends the diameter of the device is greater than at the ends and/or at a majority of the windings, such that at each such location a circumferential bulge of the otherwise cylindrical shape is created. The invention is also directed to an insertion system which comprises the device, or stent, as described above and a suitable means for delivering the device to a constricted area in a stressed or torqued condition where the device's profile has been reduced. Then, once the device is in position, the ends of the device are released and the device returns to its larger diameter, larger profile condition.

These and further features of the invention will become clear from the following detailed description which refers to the drawings herein. In the embodiment of the invention shown in FIGS. 1 and 2, a spatial spiral (helix) is wound of wire of a material tolerated by the human body and which, furthermore, is not corroded or otherwise attacked by body liquids. Such a material, also known as a physiologically or medically acceptable material, could be one or more of several materials known for this purpose. Especially useful here are metals such as medical grade stainless steel, gold-plated medical grade stainless steel, stainless steel coated with silicone, bicarbon, or polytetrafluoroethylene, such as TEFLON®, tantalum, titanium, or nickel-titanium alloy, such as Nitinol, or bioabsorbable material. The wire typically has a diameter of from about 0.1 to 1.0 mm, preferably from about 0.15 to 0.60 mm. It is important that the winding be sufficiently tight that the outer surface of the device is substantially continuous, thus preventing "leaking through" of the inner lining of a vessel or duct. However, in cases in which incorporation of the stent into the wall of a duct is preferred, space of about 0.1 to 2.0 mm will be left between the loops of the coil.

The outer diameter and length of the device will vary according to the intended use. For prostatic or urinary use, the outer diameter of the wound device will typically be from about 10 to 40 French (from about 3.3 to 13.3 mm), and the length of the device can vary from about 2 to 15 cm, preferably from about 4 to 12 cm. It is also within the scope of the invention that the device may comprise two spirals connected by a wire, the spirals and wire preferably being a continuous wire.

Figure 1A:
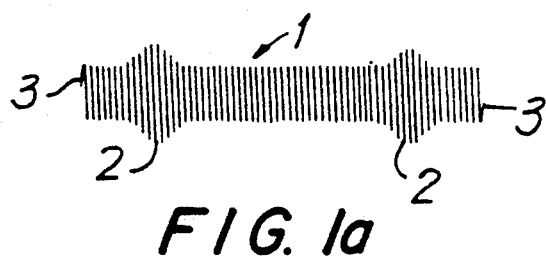
FIGS. 1a, 1b, and 1c represents schematic lateral views of different embodiments of the invention in relaxed, non-torqued condition.
Figure 1B:
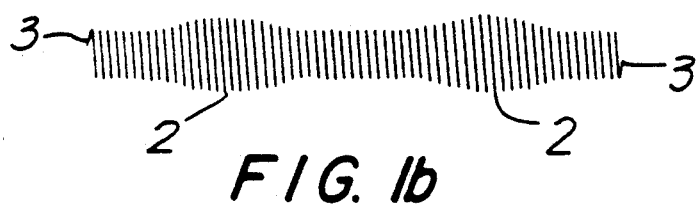
Figure 1C:

In FIGS. 1a, 1b, and 1c the windings of the helix of the spiral 1 at two locations 2 intermediate the two ends thereof are of successively increasing/decreasing diameter. Each increased winding, or bulge, 2, relative to the major part of the helix creates an outward bulge of the device, the purpose of which will become clear. The number of such bulges 2 need not be two; there may be one such location of increased diameter or more than two, as shown in FIG. 1c, or even no bulges at all.

Rotating the respective ends of the helical spiral 1 in opposite directions causes its total length to increase, resulting in a decrease of the diameter of the stent and its bulges.

The bulges of the device are significant in assisting the device to maintain its relative position within a body vessel, channel, or duct. While non-expandable cylindrical devices would tend to reposition themselves due to body movement and/or fluid flow, devices with bulges tend to remain in position or move only slightly. The pressure exerted radially by the bulges as well the overall radial pressure from the spiral tend to anchor the device within a passageway At both ends of the spiral 1 there are provided very small hooks, rings, or balls 3. Hooks or rings can result from, for example bending of the free ends of the wire of which the spiral 1 is wound, and balls can be formed from soldering or melting the ends of the wires. The balls will typically have a diameter of from about 0.2 to 5 mm. It is within the scope of the invention that these attachments 3 could also comprise hooks, rings, balls, or similar means affixed to the wire.

Figure 2A:
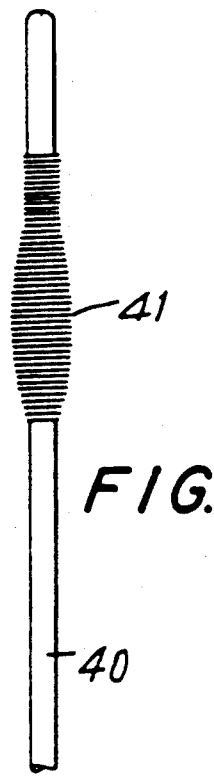
FIG. 2a represents a schematic lateral view of an embodiment of the invention positioned in torqued, stressed condition on a delivery means.
Figure 2B:
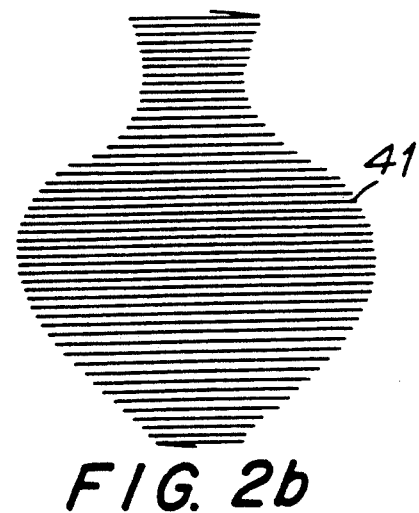
FIG. 2b represents schematic lateral view of a further embodiment of the invention in relaxed, non-torqued condition.

FIG. 2b shows another embodiment according to the invention constituting a spatial spiral with windings gradually increasing and then decreasing. In this way the device is given an amphora-like outline. In FIG. 2a this device is stretched on an insertion member 40, which will be described more fully below.

Figure 3:
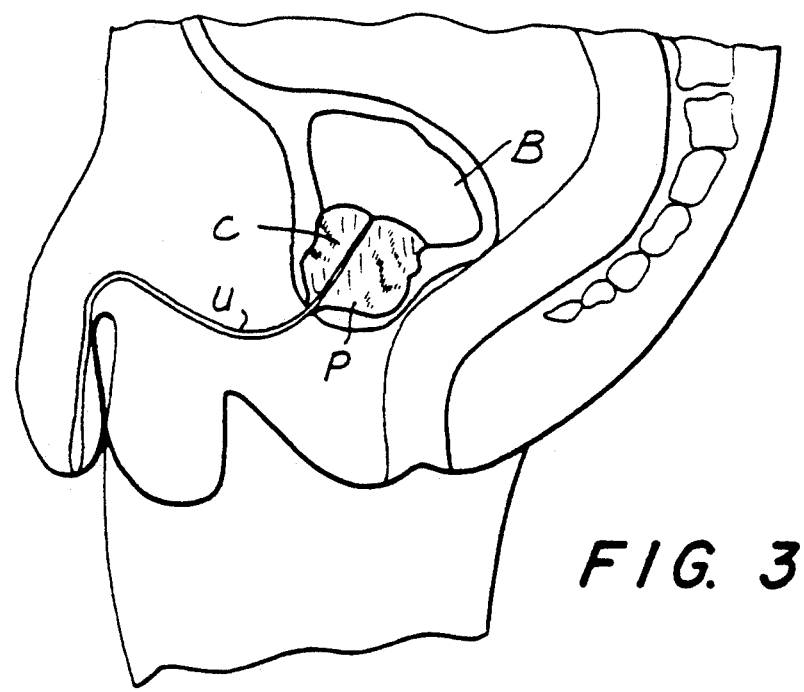
FIG. 3 represents a simplified cross-sectional view of a male pelvis illustrating a stenotic condition of the urethra.

In FIG. 3 the bladder of a male person is seen indicated by B. From the bladder B leads the urethra U, which due to hypertrophy of the prostate P has become constricted at C resulting in total stenosis.

Figure 4:
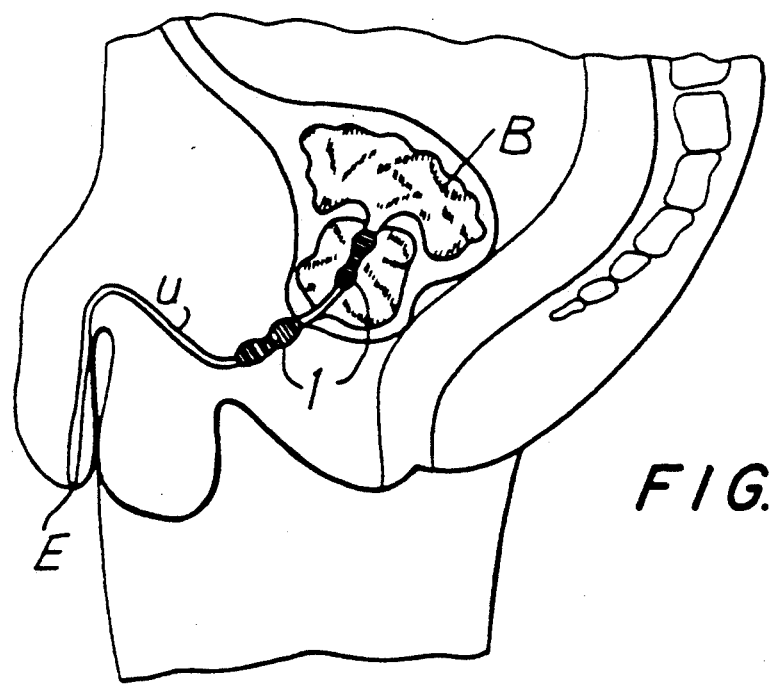
FIG. 4 represents a simplified cross-sectional view similar to FIG. 3 showing an embodiment of the invention placed in the prostatic and anterior urethra.
Figure 4A:
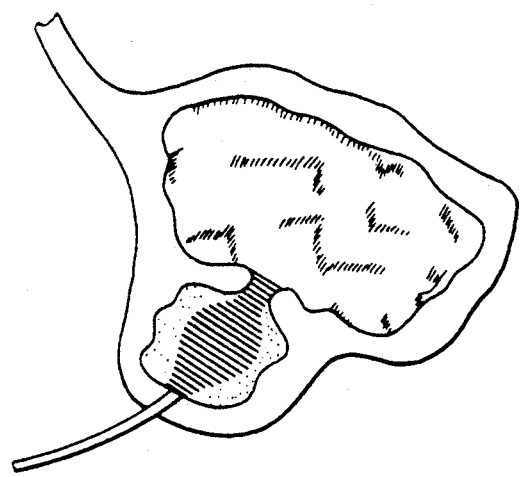
FIG. 4a represents a schematic cross-sectional view showing the embodiment of FIG. 2b as positioned in the prostatic section of the urethra.

According to FIG. 4 the stenotic condition has been remedied by insertion of the spatial spiral 1 into the prostatic urethra, or the stenotic urethra, ensuring unimpeded flow of urine from bladder B to the natural exit E through the urethra U.

The circumferential bulges (see FIGS. 1a, 1b, and 1c) also seen in FIG. 4 prevent the spiral 1 from becoming dislocated within the urethra, because the larger diameter of the spiral bulges firmly anchor the spiral in situ.

The device shown in FIGS. 2a and 2b is intended to use for opening the prostatic urethral lumen to a very large diameter, e.g., 30 to 40 mm, resulting in devulsion of prostatic commissures and exerting pressure atrophy on the gland tissue which results in increased prostate urethral diameter.

According to another aspect of the invention, the devices or stents are inserted into a corpeal channel or passageway using special means for that purpose, the device and the insertion means becoming an insertion or delivery system. Since the diameter of the device will be greater than, for example, the urethral lumen, the diameter of the device must be reduced to eliminate trauma as the device is inserted. Apparatus and methods of reducing the diameter and inserting the device into the respective body duct have been developed.

Figure 5:
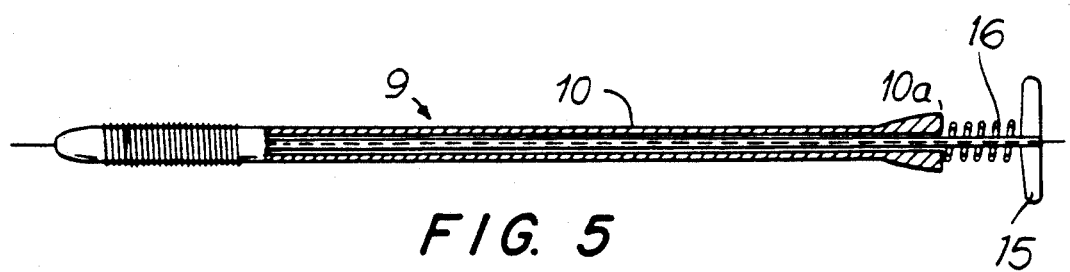
FIGS. 5 and 5a represent cross-sectional lateral views of delivery means for inserting stents of the invention into the urethra.
Figure 5A:
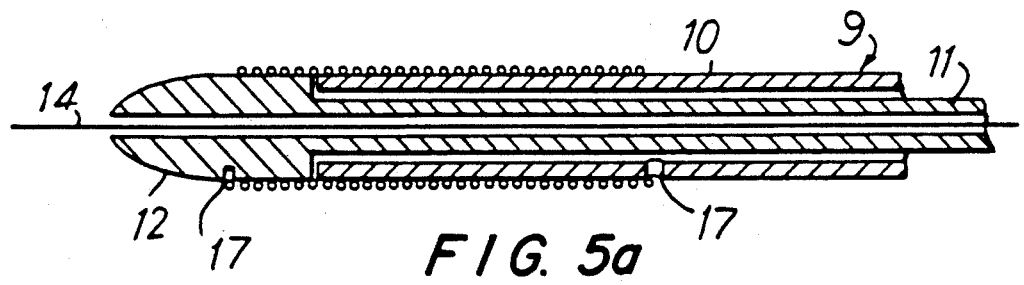

An instrument for inserting the new device into a fluid conducting conduit in the human body, e.g., into the urethra of a person, is shown in FIGS. 5 and 5a. The instrument 9 comprises two elongated tubes telescoping into one another. In the outer tube 10 is held an inner tube 11 (see FIG. 5a) having a head portion 12. The axial bore of tube 11 and of the head portion 12 are co-extensive and throughout the length of these combined bores extends guidewire 14, i.e., a flexible wire or thin rod, the primary purpose of which is to guide the instrument 9 to a constriction. At the outermost end 10a of tube 11 is provided a grip 15. Between grip 15 and a thickened end 10a of tube 10 a pressure spring 16, which abuts with both its ends on the grip 15 and the end phase 10a of tube 10, is slipped on tube 11. This spring 16 also acts as a locking means preventing the rotated spiral from returning spontaneously to its initial diametrical state.

For insertion of the spiral 1 into the respective duct, the spiral 1 is slipped onto the instrument 9 shown in FIG. 5 and FIG. 5a, covering part of the head portion 12 and the forward or distal end of tube 10. The small hooks 3 on the spiral 1 are received in holes 17 in the head position 12 of the tube 10, thereby immobilizing the helix 1 on the instrument 9. As the inner tube 11 is turned by means of grip 15 in counterclockwise direction, the spatial spiral 1 is axially extended, i.e., lengthened, and the spiral diameter is consequently reduced.

In this condition of reduced diameter the attending physician or surgeon can insert the instrument into the urethra (or any other duct) while viewing the position through x-ray or by endoscopy or ultrasonography.

As soon as the spiral arrives at the stenotic region, the physician imparts clockwise turns to grip 15, slowly enlarging the spiral diameter and thereby freeing the spatial spiral from the instrument and leaving the spiral 1 in the urethra, widening the stenotic portion thereof. Due to the elastic properties of the spiral winding, the spiral diameter, including that of the bulges 2, revert to the condition of FIG. 1, preventing the spiral 1 from becoming displaced.

The inner axial space of the tube 11 makes it possible to the physician or surgeon to insert the combined tubes 10 and 11, guiding them along the guidewire 14 previously inserted into the patient's stenotic duct. Thus, this method ensures a directed insertion of the device with minimal probability of damage or perforation of the respective duct.

Figure 7B:
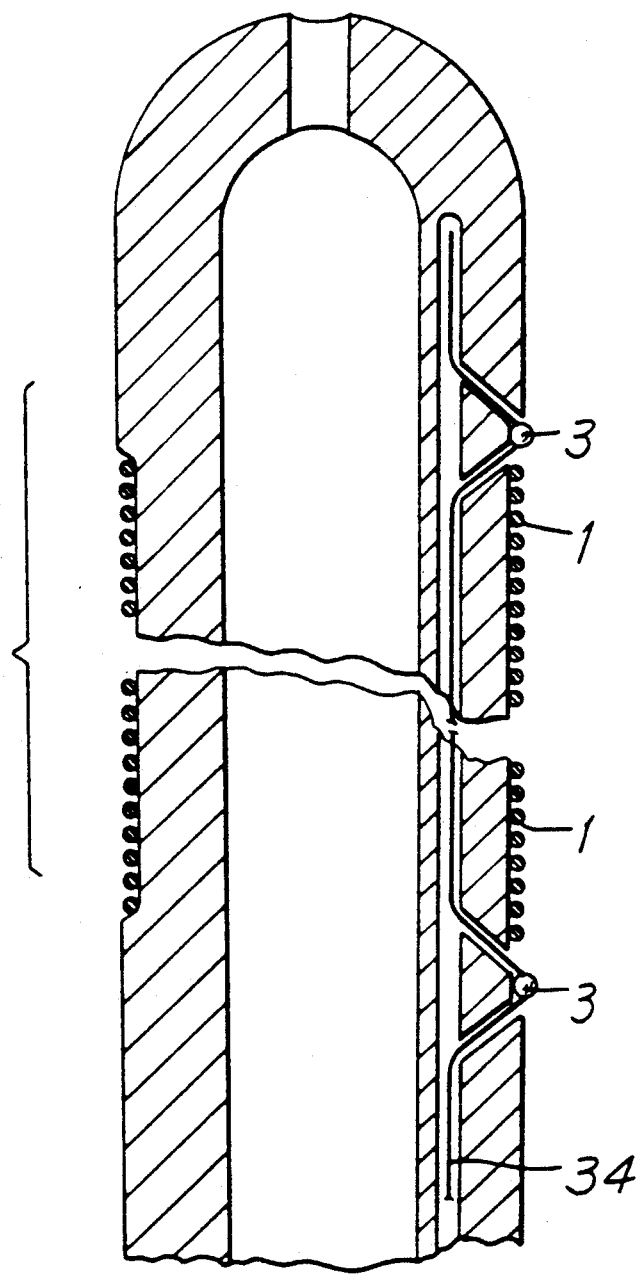
FIGS. 7b and 7c represent lateral and cross-sectional views of the locking and release mechanism of a stent of the invention mounted on a delivery catheter.

As a further example, there is shown in FIGS. 7 and 7a an insertion instrument 39 comprising a semi-stiff tube 30 having an end piece 31 for the connection to tube 30 of whatever auxiliary instrument of known kind, such as an irrigation syringe, and a head portion 32 with openings 32a, 32b, and 32c. A flexible guidewire (not shown) can extend throughout the length of tube 30 and through opening 32a.

A wire 34 keeps the spiral 1 at reduced diameter as it extends through one or more openings, such as 32b and 32c, and keeps the two small terminal rings or balls 3 of the spiral 1 pushed against the introducing instrument wall (see FIGS. 7, 7a, 7b, and 7c). The balls prevent rotational discharge of the stent because the ball cannot pass under the wire 34 because its diameter is larger than the distance between the external wall of the introducing instrument and the wire 34. The instrument is introduced into the urethra in the same way as described in connection with the other instruments mentioned above. As soon as it is at the stenotic region, handle 35 is rotated or withdrawn to pull out the wire 34 to free the spiral terminals 3, resulting in radial pressure and rotational movement of the spiral 1, which continues until it reaches its initial, larger diameter. The introducing instrument is now pulled out, leaving the spiral in the stenotic region.

Figure 7C:
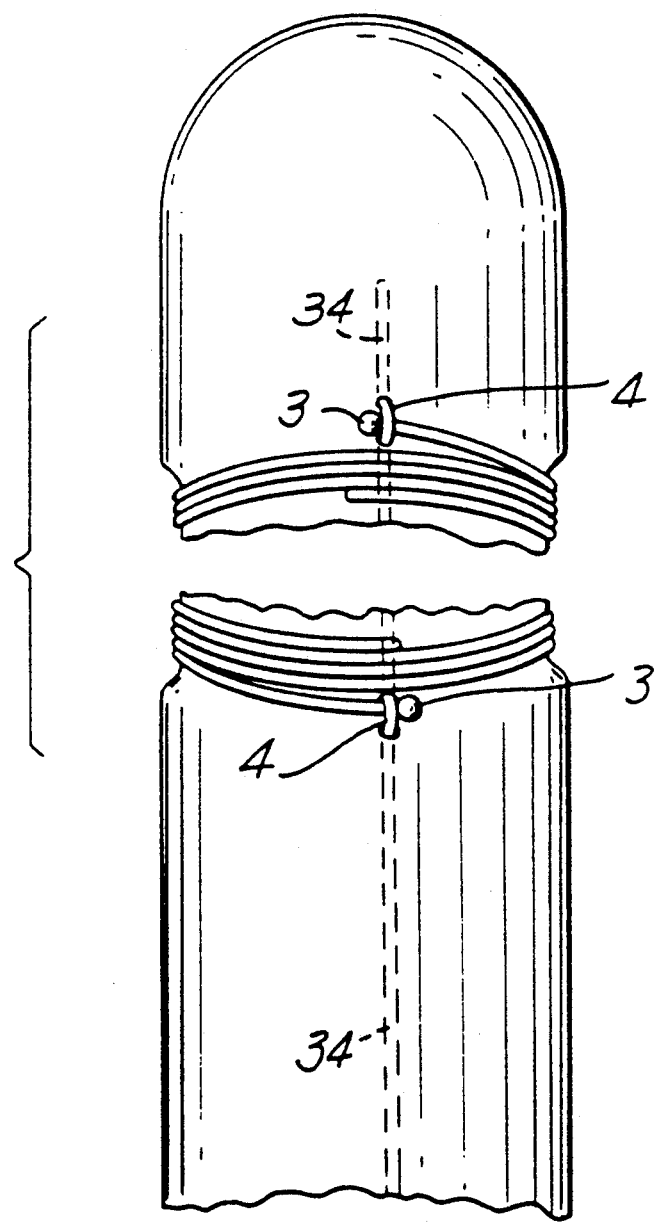

It is within the scope of the invention that there may be variations of the releasable locking system shown in FIGS. 7 to 7c. Any system wherein ends of the spiral 1 would be constrained when the spiral is wound or constricted but released by a remotely, proximally operated mechanism, would be suitable. For example, rings or balls 3 might be held within the introducing instrument rather than on its exterior surface.

Figure 6:
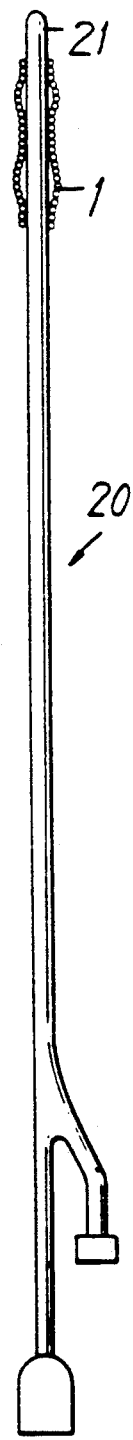
Figure 6A:
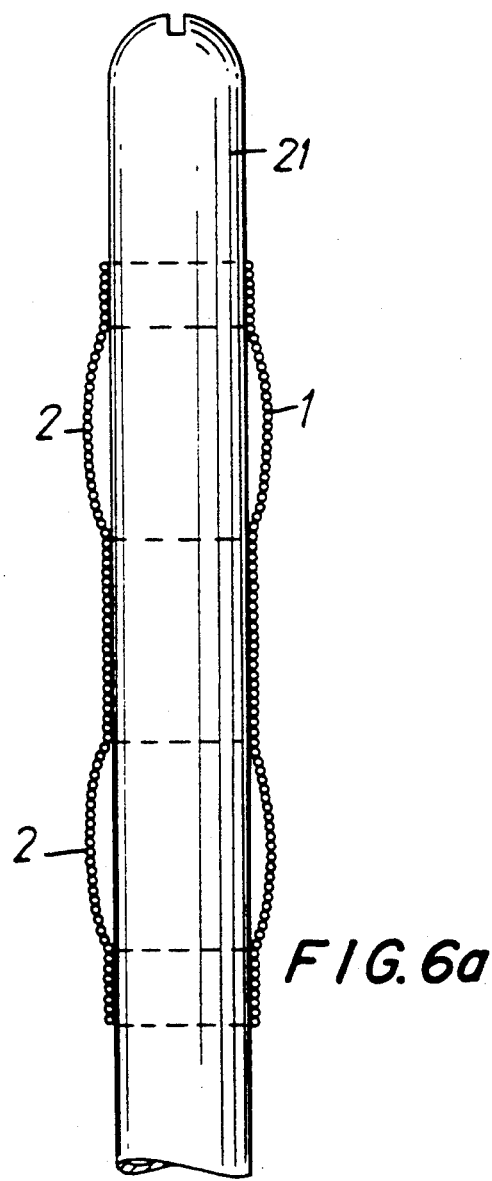

FIG. 6 illustrates another method of introducing the spiral into a body duct, similar to conventional catherization of the urethra or blood vessels. The balloon catheter 20 is of generally known type of polymeric catheter, which would be known to those in the art and really does not require extensive description. At the distal end 21 of the catheter 20 the spiral 1 is slid thereon, as shown at enlarged scale in FIG. 6a. The spiral stent diameter is reduced to facilitate insertion into the urethra and return to initial diameter once the balloon is deflated (see FIG. 6a). In this method the spiral is mounted on the catheter when the spiral is in condition of reduced diameter. In that position it is slipped onto the catheter balloon, and when the balloon is inflated, the circumferentially acting forces squeeze the spiral wire. These frictional forces are greater than those urging the spring 16 to rotate. As long a the balloon is in inflated condition, the spiral stays at smaller diameter and is so inserted. With slow deflation of the balloon the spiral slowly reverts to large diameter, and the catheter is withdrawn.

The way of introducing a generally known catheter into the urinary tract of a person (or any other body conduit) is well known and does not require any elaborate explanatory information.

A further example for insertion of the new device comprises endoscopic insertion of the spiral. In that method the spiral in the state of reduced diameter is inserted into, i.e., within, an endoscopic tube. When the endoscopic distal opening is positioned in the stenotic region, the spiral is pushed out of the endoscopic tube with the aid of a special push instrument located in the endoscopic tube. As the spiral is pushed from the endoscope, it regains its initial, larger diameter, whereupon the endoscope is removed.

The insertion of the device according to FIGS. 2a and 2b is performed by use of an insertion catheter 40 onto which the device 41 is wound in extended condition. The insertion with the aid of a catheter is preferable to that of balloon dilation of the prostate since it can be performed without requiring anesthesia and remains active for a relatively long period (up to several days) and causes pressure atrophy, a method which cannot be applied at balloon dilation of the prostate due to the short duration of the procedure.

In all cases the attending medical practitioner will choose the instrument which in his judgment is the most appropriate of the case.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A medical device for opening constrictions in conduits in the body of humans or animals, comprising a spatial spiral of elongate axial extension wound of thin wire and having attachment means at each distal end, to hold the spiral when wound in a constricted condition and to permit self-expansion when the attachment means are released, wherein at one or more locations intermediary of the two ends of the spiral the diameter of the spiral is greater than the major part of the windings, such that at each such location a circumferential bulge of the otherwise cylindrical shape of the device is created.

2. The device of claim 1, wherein there are two bulges.

3. The device of claim 1, wherein the device has an amphora-like outer shape.

4. The device of claim 1, wherein the spatial spiral is wound of wire that is physiologically acceptable.

5. The device of claim 4, wherein the wire is selected from the group consisting of medical grade stainless steel, gold-plated medical grade stainless steel, medical grade stainless steel coated with silicone, biocarbon, or polytetrafluoroethylene, tantalum, titanium, nickel-titanium, bioabsorbable materials, and other medically implantable materials.

6. The device of claim 1, wherein the windings of the helix at two locations intermediate the two ends thereof are of successively increasing/decreasing diameter.

7. A system for implanting a device to open constrictions in corporal conduits, which comprises (a) an elongated tubular member comprised of an inner tube and an outer tube slidably and concentrically positioned around at least a portion of said inner tube and (b) a spatial spiral of elongate axial extension wound of thin wire and having proximal and distal ends with attachment means at each end, wherein said spiral is positioned on and concentric to said elongated tubular member, one end of the spiral is secured on each of said inner and outer tubes, respectively, said spiral is in a constricted condition such that its lateral profile is smaller than it would be if said spiral were not constricted, and said spiral is capable of being released from the elongated tubular member by rotating one of the inner an outer tubes relative to the other one.

8. The system of claim 7, wherein the elongated tubular member has openings in which the ends of the spiral are removably secured.

9. A method of opening a constriction in a body duct which comprises the steps of:

(a) inserting a system for implanting a device to open constrictions in corporal conduits, which comprises (a) an elongated tubular member comprised of an inner tube and an outer tube slidably and concentrically positioned around at least a portion of said inner tube and (b) a spatial spiral of elongate axial extension wound of thin wire and having proximal and distal ends with attachment means at each end, wherein said spiral is positioned on and concentric to said elongated tubular member, one end of the spiral is secured on each of said inner an outer tubes, respectively, said spiral is in a constricted condition such that its lateral profile is smaller than it would be if said spiral were not constricted, and said spiral is capable of being released from the elongated tubular member by rotating one of the inner and outer tubes relative to the other one;

(b) rotating one of the inner and outer tubes relative to the other one to disengage the spatial spiral from the elongated tubular member; and (c) removing the elongated tubular member from the body in the proximal direction.

10. A system for implanting a device to open constrictions in corporal conduits, which comprises (a) an elongated tubular member and (b) a spatial spiral of elongate axial extension wound of thin wire and having proximal and distal ends with attachment means at each end, wherein said spiral is positioned on and concentric to said elongated tubular member, said spiral is in a constricted condition such that its lateral profile is smaller than it would be if said spiral were not constricted, and the elongated tubular member is a balloon dilatation catheter in which the balloon is sufficiently inflated to hold said spiral in its smaller profile.

11. A system for implanting a device to open constrictions in corporal conduits, which comprises (a) an elongated tubular member and (b) a spatial spiral of elongate axial extension wound of thin wire and having proximal and distal ends with attachment means at each end, wherein said spiral is positioned on and concentric to said elongated tubular member, said spiral si in a constricted condition such that its lateral profile is smaller than it would be if said spiral were not constricted, the respective ends of the spiral wire each form a ball, and the elongated tubular member has (1) two openings into which the wire ends and balls are positioned when the spiral is in a constricted condition and (2) a release wire extending therethrough, such that each ball fits under a portion of the release wire to secure that ball and that end of the spiral wire and such that when the spiral wire is pulled proximally and longitudinally the balls and the spiral wire ends are released to permit the lateral profile or diameter of the spatial spiral to spontaneously increase by unwinding.

12. The system of claim 11, wherein the wire extends proximally from the elongated tubular member.

* * * * *